(12) United States Patent
Lu (10) Patent No.: US 11,045,347 B2
(45) Date of Patent: Jun. 29, 2021

(54) ARTIFICIAL STOMA DEVICE

(71) Applicant: Kaohsiung Chang Gung Memorial Hospital, Kaohsiung (TW)

(72) Inventor: Chi-Tung Lu, Kaohsiung (TW)

(73) Assignee: Kaohsiung Chang Gung Memorial Hospital, Kaohsiung (TW)

( * ) Notice: Subject to any disclaimer, the term of this patent is extended or adjusted under 35 U.S.C. 154(b) by 185 days.

(21) Appl. No.: 16/291,205

(22) Filed: Mar. 4, 2019

(65) Prior Publication Data
US 2020/0281759 A1 Sep. 10, 2020

(51) Int. Cl.
*A61F 5/445* (2006.01)
*A61F 5/44* (2006.01)

(52) U.S. Cl.
CPC ............ *A61F 5/445* (2013.01); *A61F 5/4408* (2013.01)

(58) Field of Classification Search
CPC ...... A61F 5/4404; A61F 5/4405; A61F 5/407; A61F 5/4408; A61F 5/441; A61F 5/442; A61F 5/443; A61F 5/445; A61F 5/448; A61F 2005/4415; A61F 2005/4455; A61F 2/02–07; A61F 2002/045; A61M 27/00; A61B 2017/00818; A61B 2018/00494; A61B 2017/12086; A61B 2017/00876; A61B 17/1707; A61B 17/52; A61B 17/7016; A61B 34/73
See application file for complete search history.

(56) References Cited

U.S. PATENT DOCUMENTS

| | | | |
|---|---|---|---|
| 3,395,710 A * | 8/1968 | Stratton | A61J 15/0049 604/270 |
| 2011/0040231 A1* | 2/2011 | Gregory | A61F 5/445 604/8 |
| 2015/0057626 A1 | 2/2015 | Hanuka et al. | |

FOREIGN PATENT DOCUMENTS

| CN | 203417399 U | 2/2014 |
|---|---|---|
| WO | 03032878 A1 | 4/2003 |

OTHER PUBLICATIONS

Search Report appended to an Office Action, which was issued to Taiwanese counterpart application No. 107126069 by the TIPO dated Jun. 11, 2019 (2 pages, English translation included).

* cited by examiner

*Primary Examiner* — Nicholas J Weiss
*Assistant Examiner* — Eric Rassavong
(74) *Attorney, Agent, or Firm* — Michael Best & Friedrich LLP (57) ABSTRACT

An artificial stoma device includes a solid unit and a hollow unit. The solid unit includes a blocking member that is adapted to block off a downstream section of an intestine and that has a contacting face adapted for facing an upstream section of the intestine, and a first connecting member that is connected fixedly to the contacting face of the blocking member. The hollow unit includes a conduit that has an outer surrounding surface and two opposite conduit openings being adapted to be disposed respectively at the upstream section of the intestine and an opening of a skin tissue, and a second connecting member that is connected fixedly to the outer surrounding surface and that is detachably connected to the first connecting member of the solid unit.

7 Claims, 7 Drawing Sheets

ARTIFICIAL STOMA DEVICE

FIELD

The disclosure relates to an artificial organ, and more particularly to an artificial stoma device.

BACKGROUND

An artificial stoma is an opening of a severed intestine formed as a substitute for excretion when a part of the intestine is cut off due to lesions in the intestine of a patient. In general, an artificial stoma serves as a replacement of a downstream section of the intestine after it is removed, or as a temporary replacement of the downstream section of the intestine as it is recovering.

Figure 1:
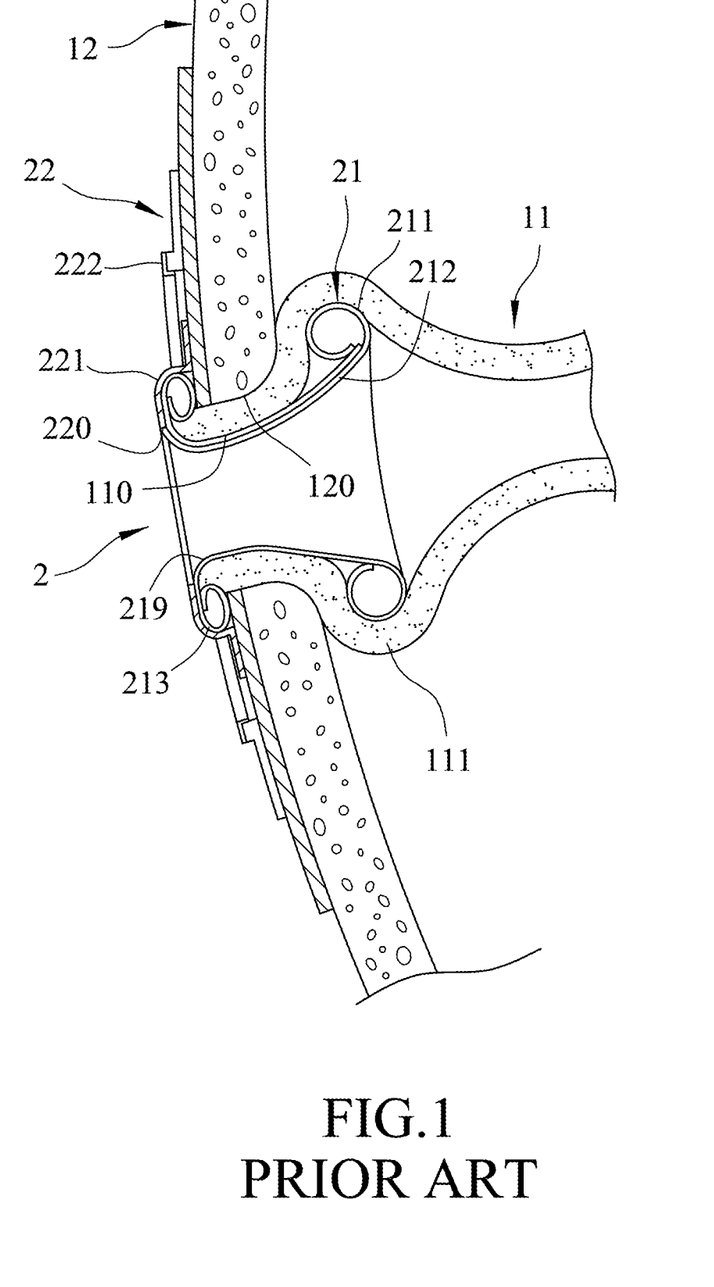
FIG. 1 is a fragmentary sectional view illustrating a conventional artificial stoma device connecting an intestine to a human abdomen.

Referring to FIG. 1, a conventional artificial stoma device 2 is adapted to be installed in a first opening 110 formed in a severed intestine 11 and in a second opening 120 formed in a human body 12. The intestine 11 extends from the inside to the outside of the second opening 120 in such a way that the first opening 110 faces outwardly. The artificial stoma device 2 includes a brace member 21 adapted to be disposed in the first opening 110 of the intestine 11, and a positioning member 22 connected to an outer portion of the brace member 21.

The brace member 21 is hollow and includes an inner ring 211 that is adapted to abut against an inner wall of the intestine 11, an extension tube 212 that is connected to the inner ring 211 and that has a cross-section decreasing in a direction away from the inner ring 211, and an outer ring 213 that is connected to an end of the extension tube 212 opposite to the inner ring 211, and that defines an aperture 219. The positioning member 22 is adapted to be attached to the skin of the human body 12, and includes an annular portion 221 that defines an annular hole 220, and a plate portion 222 that is adapted to be attached to the human body 12. The inner ring 211 has a diameter larger than that of the outer ring 213. When the brace member 21 is disposed inside the intestine 11, a portion 111 of the intestine 11 is expanded by the inner ring 211. The outer ring 213 surrounds the first opening 110 of the intestine 11, and the aperture 219, the intestinal tract of the intestine 11, and the external environment are in spatial communication with each other. The outer ring 213 abuts against the outside of the human body 12, while the inner ring 211 abuts the portion 111 of the intestine 11 against the inner surface of the human body 12, so that the intestine 11 is positioned at the second opening 120. Then, the annular portion 221 of the position member 22 is attached to the outer ring 213 of the brace member 21, while the plate portion 222 is attached to the peripheral area of the second opening 120, so that the brace member 21 is positioned by the positioning member 22. At this point, the aperture 219 is spatially communicated with the space outside the human body 12 via the annular hole 220, and excrement transported by the intestine 11 can be discharged via the aperture 219.

Figure 2:
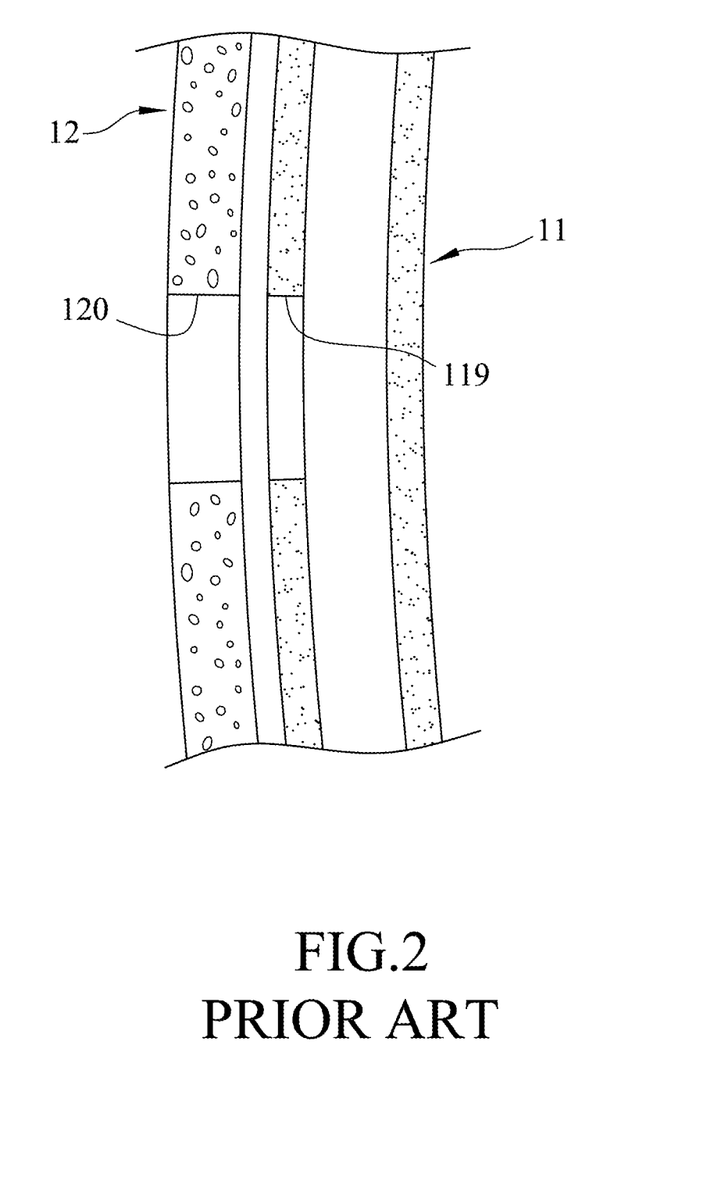
FIG. 2 is a fragmentary sectional view illustrating a setup of forming a side opening in the intestine.

However, besides the abovementioned approach for treating the severed intestine 11, in cases of temporary disposal, a setup in FIG. 2 may be adopted in order to prevent the downstream section of the intestine 11 from becoming necrotic, that is, forming a side opening 119 in the wall of the intestine 11 instead of severing the intestine 11 so that the intestine 11 may continue its normal physiological circulation. When the downstream section of the intestine 11 relative to the side opening 119 has fully recovered, the intestine 11 may be returned to its normal functioning state.

However, the artificial stoma device 2 shown in FIG. 1 is not applicable to the setup shown in FIG. 2. If the intestine 11 is directly sutured to the human body 12 such that the side opening is directly connected to the second opening 120 to form an artificial stoma, the excrement may still be transported from the upstream section to the downstream section of the intestine 11 and affect the recovery of the intestine 11. Thus, it is imperative to provide an artificial stoma device that is applicable to the setup shown in FIG. 2.

SUMMARY

Therefore, the object of the disclosure is to provide an artificial stoma device that can alleviate at least one of the drawbacks of the prior art.

According to the disclosure, the artificial stoma device is adapted to be installed in an abdomen. The abdomen contains an intestine formed with a radial side opening, and has a skin tissue formed with an opening being registered with the radial side opening. The intestine has an upstream section that is disposed upstream of the radial side opening, and a downstream section that is disposed downstream of the radial side opening. The artificial stoma device includes a solid unit and a hollow unit.

The solid unit is adapted to be inserted into the downstream section of the intestine via the opening of the skin tissue and the radial side opening of the intestine. The solid unit includes a blocking member that is adapted to block the downstream section and that has a contacting face adapted for facing the upstream section, and a first connecting member that is connected fixedly to the contacting face of the blocking member.

The hollow unit is adapted to be inserted into the upstream section of the intestine via the opening of the skin tissue and the radial side opening of the intestine. The hollow unit includes a conduit and a second connecting member. The conduit has an outer surrounding surface, and two conduit openings that are opposite to each other and that are adapted to be disposed respectively at the upstream section of the intestine and the opening of the skin tissue. The second connecting member is connected fixedly to the outer surrounding surface and is detachably connected to the first connecting member of the solid unit.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 3:
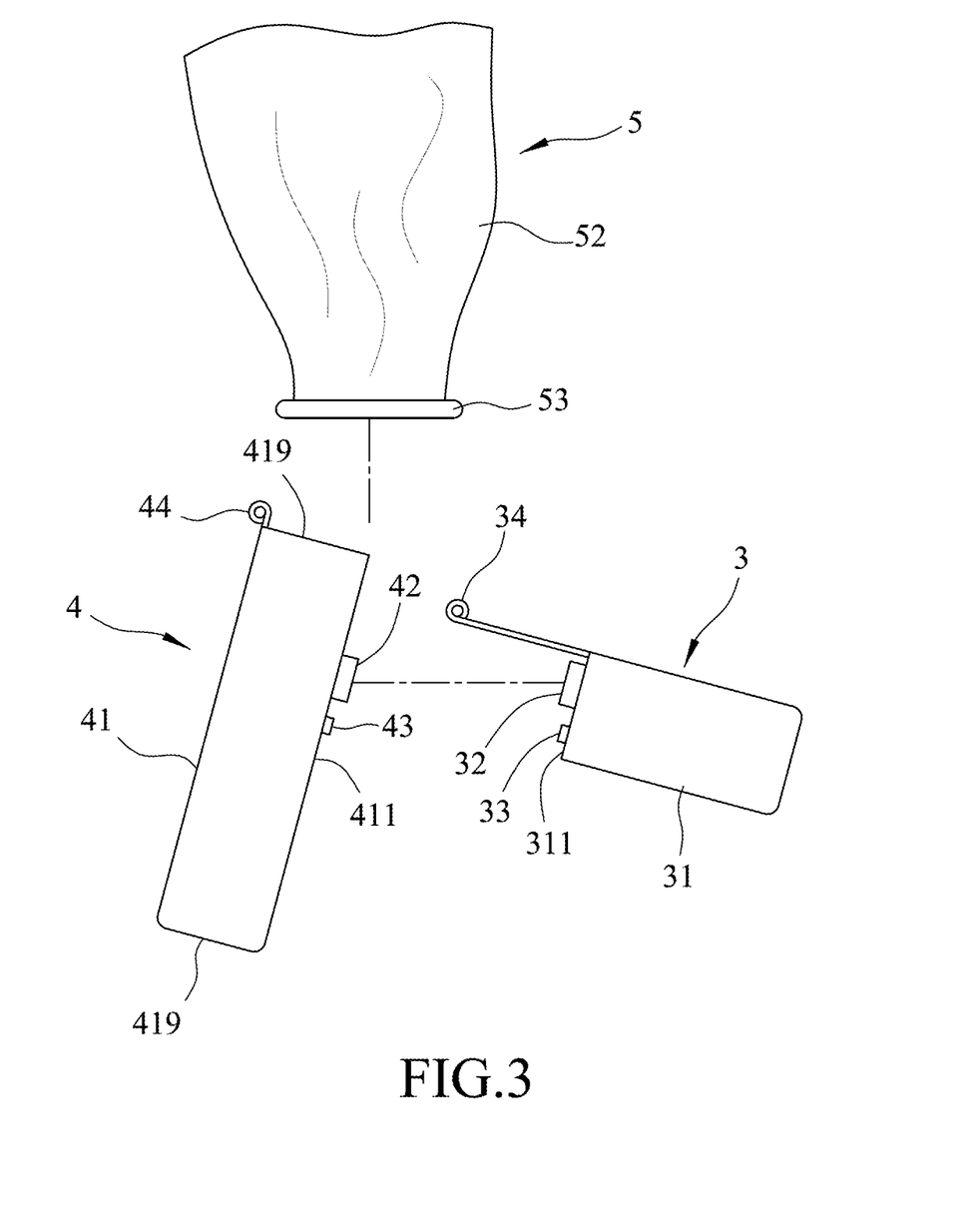
FIG. 3 is an exploded side view of an embodiment of the artificial stoma device according to the disclosure.
Figure 4:
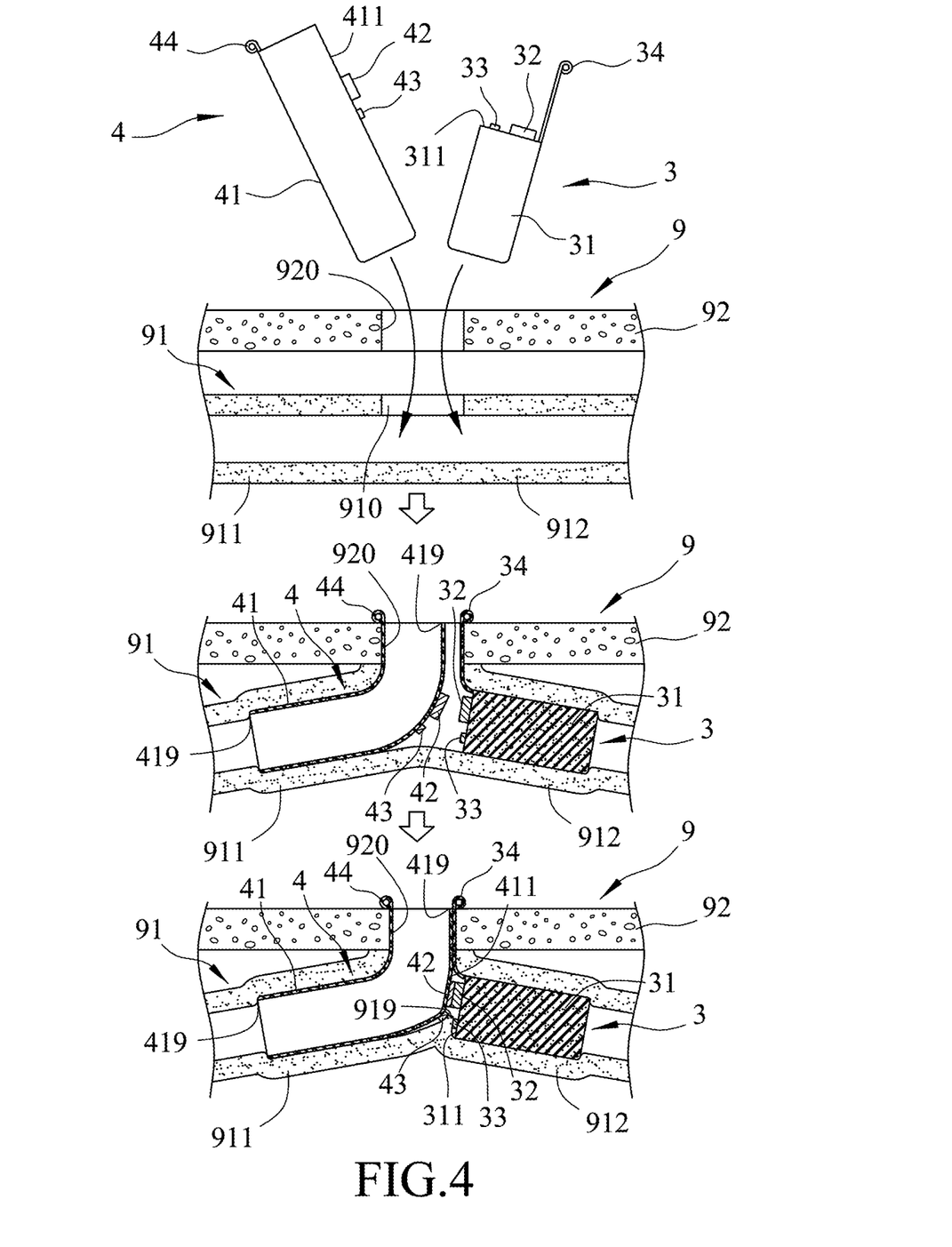
FIG. 4 is a fragmentary sectional view illustrating the installation process of the embodiment in an abdomen.

Referring to FIG. 3 and FIG. 4, an embodiment of the artificial stoma device according to the present disclosure is adapted to be installed in an abdomen 9 of a patient. The abdomen 9 contains an intestine 91 formed with a radial side opening 910, and has a skin tissue 92 formed with an opening 920 which is registered with the radial side opening 910. The intestine 91 has an upstream section 911 that is disposed upstream of the radial side opening 910, and a downstream section 912 that is disposed downstream of the radial side opening 910. Excrement of the abdomen 9 is originally transported from the upstream section 911 to the downstream section 912. The present embodiment of the artificial stoma device includes a solid unit 3, a hollow unit 4 and an outer unit 5.

The solid unit 3 is adapted to be inserted into the downstream section 912 of the intestine 91 via the opening 920 of the skin tissue 92 and the radial side opening 910 of the intestine 91. In certain embodiments, the solid unit 3 is made of medical grade silicones that are biocompatible, and that has certain flexibility and rigidity.

The solid unit 3 includes a blocking member 31, a first connecting member 32, a first fixing member 33, and a first portal member 34. The blocking member 31 is adapted to block the downstream section 912 and has a contacting face 311 adapted for facing the upstream section 911. The first connecting member 32 is connected fixedly to the contacting face 311 of the blocking member 31. The first fixing member 33 is connected fixedly to the contacting face 311 of the blocking member 31, and is spaced apart from the first connecting member 32. The first portal member 34 has an external segment adapted to be disposed outside of the opening 920, and an internal segment adapted to extend through the opening 920, and connected to the contacting face 311 of the blocking member 31. In the present embodiment, the first fixing member 33 is a magnet.

The hollow unit 4 is adapted to be inserted into the upstream section 911 of the intestine 91 via the opening 920 of the skin tissue 92 and the radial side opening 910 of the intestine 91. In certain embodiments, the hollow unit 4 is made of medical grade silicones that are biocompatible, and that has certain flexibility and rigidity.

The hollow unit 4 includes a conduit 41, a second connecting member 42, a second fixing member 43, and a second portal member 44. The conduit 41 has an outer surrounding surface 411, and two conduit openings 419 opposite to each other and adapted to be disposed respectively at the upstream section 911 of the intestine 91 and the opening 920 of the skin tissue 92. The second connecting member 42 is connected fixedly to the outer surrounding surface 411 and is detachably connected to the first connecting member 32 of the solid unit 3. The second fixing member 43 is connected fixedly to the outer surrounding surface 411 of the conduit 41, and is spaced apart from the second connecting member 42. The second portal member 44 has an external segment adapted to be disposed outside of the opening 920 and connected to the conduit 41. In the present embodiment, the second fixing member 43 is a magnet, and is to be magnetically coupled with the first fixing member 33. In this embodiment, the first connecting member 32 has an end surface distal from the contacting face 311 of the blocking member 31. The second connecting member 42 has an end surface that is distal from the conduit 41, and that has a contour identical to that of the end surface of the first connecting member 32.

Referring to FIG. 4, when the present embodiment of the artificial stoma device is to be installed in the abdomen 9, the blocking member 31 of the solid unit 3 and the conduit 41 of the hollow unit 4 are first inserted into the downstream section 912 and the upstream section 911 of the intestine 91, respectively, via the opening 920 of the skin tissue 92 and the radial side opening 910 of the intestine 91. Afterward, the end surfaces of the first and second connecting members 32, 42 are connected detachably to each other via connecting mechanisms, such as clips or snaps.

At this point, since both of the first fixing member 33 and second fixing member 43 are magnets, the first fixing member 33 and the second fixing member 43 may cooperatively clip a portion 919 of the intestine 91 (see FIG. 5) therebetween, thereby positioning the solid unit 3 and the hollow unit 4 relative to the intestine 91.

With the external segments of the first and second portal members 34, 44 being secured to an outer surface of the skin tissue 92, the first portal member 34 and the blocking member 31 cooperatively clip the skin tissue 92 and the downstream section 912 of the intestine 91 therebetween, and the second portal member 44 and the conduit 41 cooperatively clip the skin tissue 92 and the upstream section 911 of the intestine 91 therebetween. Thus, the embodiment is securely installed in the abdomen 9.

After the installation of the embodiment is completed, the two conduit openings 419 of the conduit 41 are spatially communicated with the upstream section 911 of the intestinal 91 and the opening 920 of the skin tissue 92, respectively, such that an artificial stoma is formed with the opening 920 that is in spatial communication with the upstream section 911 of the intestine 91. Thus, the excrement transported through the upstream section 911 of the intestinal 91 may be discharged from the artificial stoma, and the downstream section 912 of the intestine 91 may recover.

Figure 5:
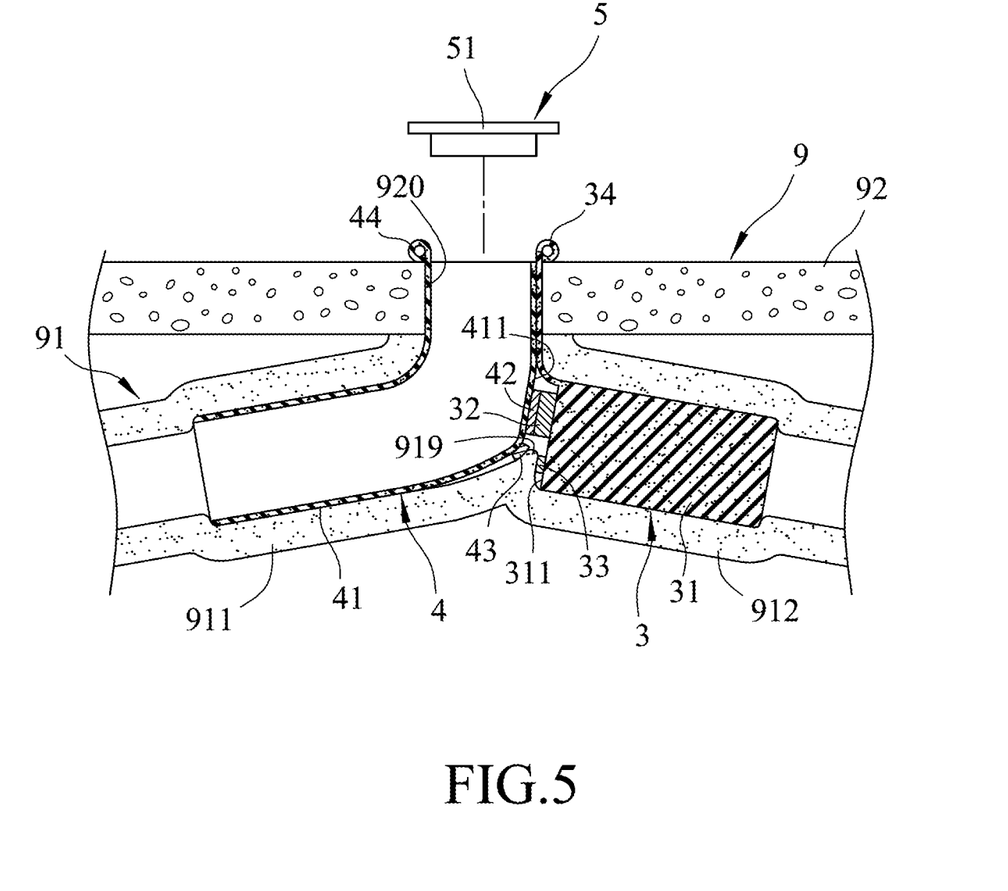
FIG. 5 is a partly exploded sectional view of a solid unit, a hollow unit, and a cover member of an outer unit of the embodiment.

Referring to FIG. 5, the outer unit 5 includes a cover member 51 adapted to cover removably the opening 920. In certain embodiments, the cover member 51 is a piece of gauze, or an object that is sterilized and that has a shielding effect. In addition to preventing direct exposure of the intestine 91 of the abdomen 9 to external environments, the cover member 51 also effectively reduces the probability of infection of the abdomen 9.

Figure 6:
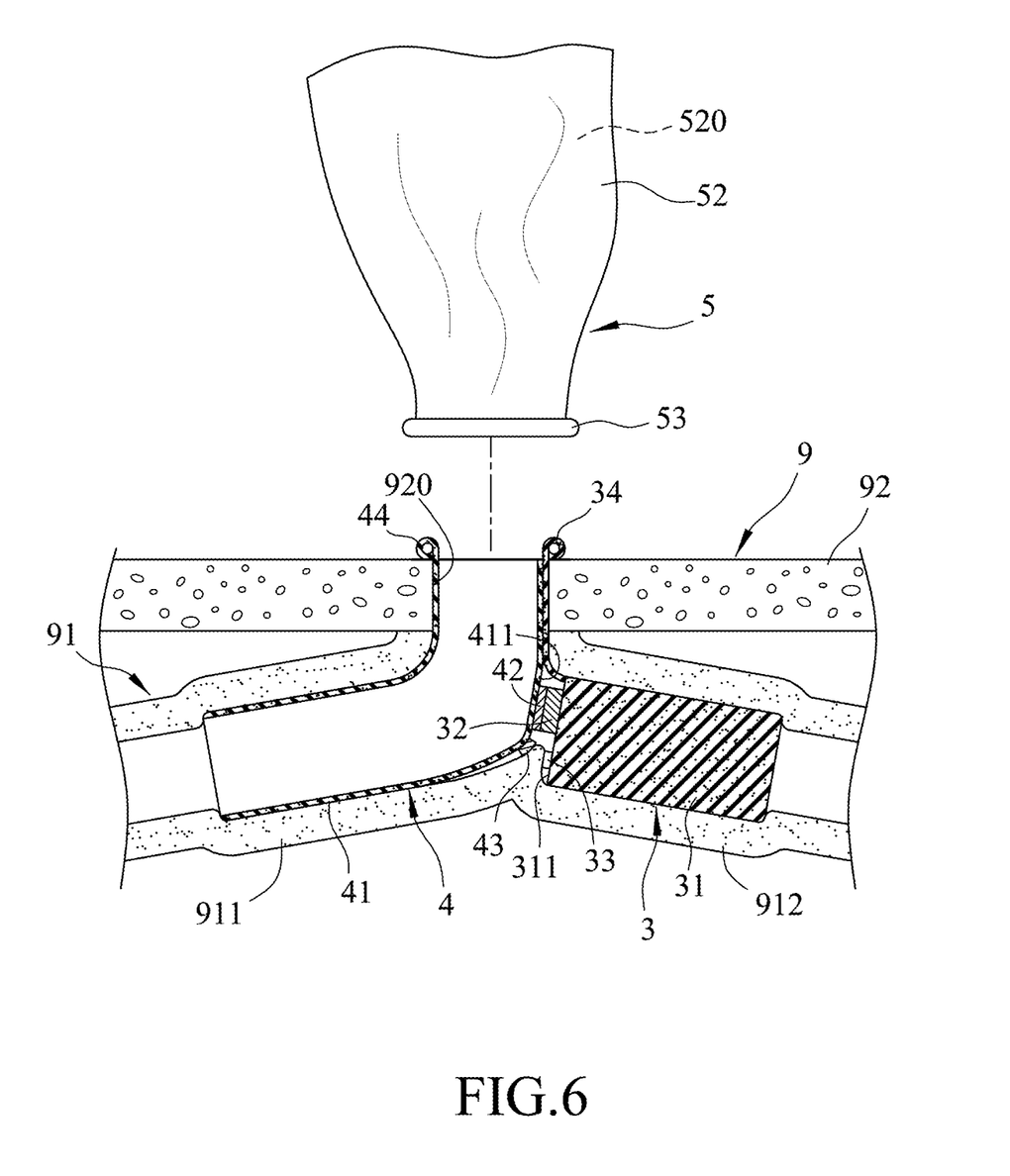
FIGS. 6 and 7 are sectional views illustrating the installation process of a pouch of the outer unit onto the solid unit and the hollow unit.
Figure 7:
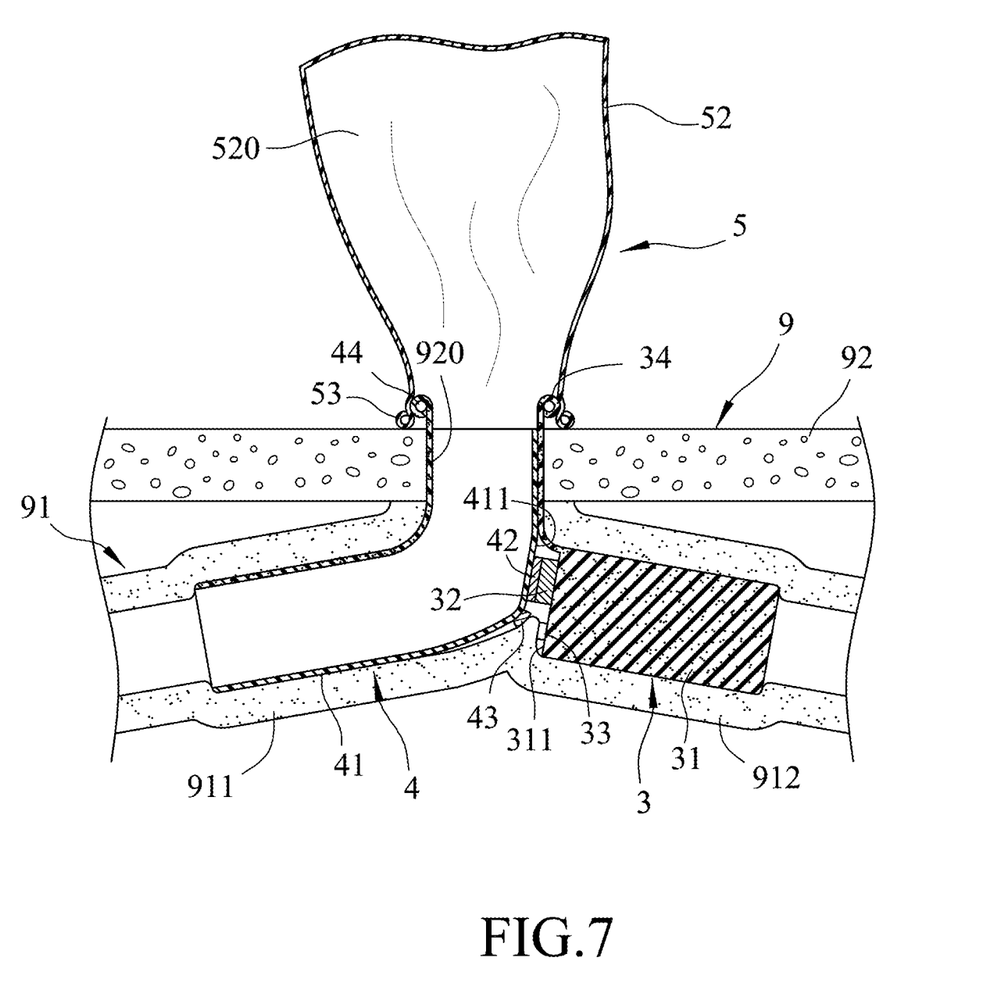

Referring to FIG. 6 and FIG. 7, the outer unit 5 further includes a pouch 52 that defines a collecting space 520, and a linking member 53 that is connected fixedly to the pouch 52 and that is connected detachably to the first portal member 34 of the solid unit 3 and the second portal member 44 of the hollow unit 4. When the pouch 52 is connected to the solid unit 3 and the hollow unit 4 by the linking member 53, the excrement discharged from the opening 920 of the skin tissue 92 is directly collected in the collecting space 520. When a patient himself/herself, a medical staff member, or a care worker intends to clean the embodiment of the artificial stoma device, the pouch 52 may be replaced simply by detaching the linking member 53 from the first portal member 34 and the second portal member 44.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An artificial stoma device adapted to be installed in an abdomen, the abdomen containing an intestine which is formed with a radial side opening, and having a skin tissue which is formed with an opening being registered with the radial side opening, the intestine having an upstream section that is disposed upstream of the radial side opening and a downstream section that is disposed downstream of the radial side opening, said artificial stoma device comprising:
    a solid unit adapted to be inserted into the downstream section of the intestine via the opening of the skin tissue and the radial side opening of the intestine, said solid unit including
        a blocking member that is adapted to block the downstream section and that has a contacting face adapted for facing the upstream section, and
        a first connecting member that is connected fixedly to said contacting face of said blocking member; and
    a hollow unit adapted to be inserted into the upstream section of the intestine via the opening of the skin tissue and the radial side opening of the intestine, said hollow unit including
        a conduit that has an outer surrounding surface, and two conduit openings being opposite to each other and adapted to be disposed respectively at the upstream section of the intestine and the opening of the skin tissue, and
        a second connecting member that is connected fixedly to said outer surrounding surface and that is detachably connected to said first connecting member of said solid unit.

2. The artificial stoma device as claimed in claim 1, wherein:
    said solid unit further includes a first fixing member that is connected fixedly to said contacting face of said blocking member, and that is spaced apart from said first connecting member;
    said hollow unit further including a second fixing member that is connected fixedly to said outer surrounding surface of said conduit, and that is spaced apart from said second connecting member; and
    said first fixing member and said second fixing member are adapted to cooperatively clip a portion of the intestine therebetween.

3. The artificial stoma device as claimed in claim 2, wherein said first fixing member of said solid unit and said second fixing member of said hollow unit are magnets.

4. The artificial stoma device as claimed in claim 1, further comprising an outer unit that includes a cover member adapted to cover removably the opening of the skin tissue.

5. The artificial stoma device as claimed in claim 1, wherein:
    said solid unit further includes a first portal member that has
        an external segment adapted to be disposed outside of the opening of the skin tissue, and
        an internal segment adapted to extend through the opening of the skin tissue, and connected to said contacting face of said blocking member;
    said first portal member and said blocking member are adapted to cooperatively clip the skin tissue and the downstream section of the intestine therebetween;
    said hollow unit further including a second portal member that has an external segment adapted to be disposed outside of the opening of the skin tissue and connected to said conduit; and
    said second portal member and said conduit are adapted to cooperatively clip the skin tissue and the upstream section of the intestine therebetween.

6. The artificial stoma device as claimed in claim 5, further comprising an outer unit including a pouch that defines a collecting space, and a linking member that is connected fixedly to said pouch and that is connected detachably to said first portal member of said solid unit and said second portal member of said hollow unit.

7. The artificial stoma device as claimed in claim 1, wherein:
    said first connecting member has an end surface distal from said contacting face of said blocking member; and
    said second connecting member has an end surface distal from said conduit, connected detachably to said end surface of said first connecting member, and has a contour identical to that of said end surface of said first connecting member.

* * * * *

UNITED STATES PATENT AND TRADEMARK OFFICE
CERTIFICATE OF CORRECTION

| | |
|---|---|
| PATENT NO. | : 11,045,347 B2 |
| APPLICATION NO. | : 16/291205 |
| DATED | : June 29, 2021 |
| INVENTOR(S) | : Lu et al. |

It is certified that error appears in the above-identified patent and that said Letters Patent is hereby corrected as shown below:

On the Title Page

Item (12) "Lu" is corrected to read --Lu et al.--.

Item (72) Inventor is corrected to read:
--Chi-Tung Lu, Kaohsiung (TW);
Chien-Chang Lu, Taichung (TW)--.

Signed and Sealed this
Fourteenth Day of June, 2022

Katherine Kelly Vidal
*Director of the United States Patent and Trademark Office*